United States Patent [19]

Brous

[11] 4,134,834

[45] Jan. 16, 1979

[54] HEMODIALYSIS APPARATUS

[75] Inventor: Donald Brous, Manchester, N.H.

[73] Assignee: Artificial and Transplant Organs, Inc., Manchester, N.H.

[21] Appl. No.: 646,765

[22] Filed: Jan. 6, 1976

[51] Int. Cl.² .......................................... B01D 31/00
[52] U.S. Cl. ................................... 210/127; 210/128; 210/140; 210/321 B
[58] Field of Search ............... 210/9.6 M, 321 B, 139, 210/140, 138, 127, 128; 137/93

[56] References Cited

U.S. PATENT DOCUMENTS

| 3,457,944 | 7/1969 | Cary et al. | 210/321 B X |
| 3,474,907 | 10/1969 | Cary et al. | 210/321 B X |
| 3,482,697 | 12/1969 | Tremont et al. | 210/140 X |
| 3,605,783 | 9/1971 | Pecker et al. | 137/93 |
| 3,774,762 | 11/1973 | Lichtenstein | 210/96 M X |
| 3,932,279 | 1/1976 | Yocum | 210/139 X |

OTHER PUBLICATIONS

Dialung, from Trans. Amer. Soc. Artif. Int. Organs, 1964.

Primary Examiner—Frank A. Spear, Jr.
Attorney, Agent, or Firm—Charles R. Fay

[57] ABSTRACT

A miniaturized proportioning system for continuously mixing and preparing dialysate in accurate proportions, as may be prescribed by a physician, for simultaneous clinical treatment of a plurality of patients, e.g., ten, or in another form for treating a single patient almost anywhere.

4 Claims, 4 Drawing Figures

HEMODIALYSIS APPARATUS

BACKGROUND OF THE INVENTION

The state of the art as it relates to proportioning or the mixing of dialysate is deficient in one or more respects in that presently known techniques require that larger volumes in excess of 50 gallons at a time be prepared. Further, in order to maintain accurate proportions of concentrate and water to prepare dialysate of proper concentration, generally rather sophisticated metering pumps actuated by electronic controls are required. This prior art technique has in the past been fairly satisfactory since much of the dialysis was done at hospitals or kidney centers where multiple patients dialysing is done and these large volumes of dialysate once prepared can be used within a reasonably short time.

However, modern technology has developed portable dialysing equipment for individual home use, accordingly requiring much smaller volumes of dialysate preparation. Obviously, the accuracy with which the concentrate is diluted to its prescribed levels remains totally important.

The present invention provides a proportioning mechanism which may easily be integrated into a portable hemodialysis system while at the same time providing the important quality of an accurate proportioning whereby to repeatedly prepare dialysate of proper concentration.

SUMMARY OF THE INVENTION

In the case of multi-patient systems, the present proportioning apparatus includes two relatively small one liter clear plastic tanks, each of which is equipped with two electrically operated inlet valves to admit simultaneously dialysate concentrate and tap water for dilution. Each tank is also equipped with an electric outlet valve to direct correctly proportioned dialysate from the tank to the patient's bedside console. The dialysate concentrate is directed to the tank from a separate container of suitable size by means of a clear plastic piston pump, equipped with a valve preventing back flow. Each dialysate proportioned tank is programmed to hold approximately one liter of the diluted concentrate between a high limit and a low limit magnetic float level switch, and the pump is set to meter approximately 30 mls. of concentrate.

The pump meters the prescribed amount of the dialysate concentrate into one of the two proportioning tanks and simultaneously tap water rapidly enters the tank and mixes with the concentrate to make up a one liter batch.

When the proportioning of the dialysate is completed, the outlet valve opens and the pump sucks proportioned dialysate out of the tank propelling it through a conductivity monitor and a three way valve to the patient's bedside console.

While one proportioning tank is emptying, the second proportioning tank is charged with dialysate concentrate and water in the manner described to prepare a second tank of proportioned dialysate. When the dialysate level in the first tank reaches its low level point, an electrical signal closes its outlet valve and at the same time opens the outlet valve on the second tank so that the pump sucks out the second batch of dialysate with no interruption in operation. The switching back and forth continues automatically and continuously as the proportioning tanks alternately fill and empty.

The single patient system is portable and includes a single tank that fills simultaneously with tap water and with a metered amount of dialysate concentrate. This tank holds approximately one liter between high limit and low limit float level swtiches and the pump is set to meter out approximately 30 mls. of concentrate.

The concentrate pump commences its stroke when the lower float switch is raised above the "filled" level by the incoming water forming concentrate for approximately three seconds, and then continuing to operate for an additional three seconds to return to its original position. That is, the pump has a six second 360° cycle delivering dialysate concentrate during the first half of the cycle, then refilling with concentrate during the second half of the cycle. When the tank is filled with proportioned dialysate to the cutoff level, the upper magnetic float switch shuts off the water inlet solenoid valve.

PREFERRED EMBODIMENT OF THE INVENTION

Figure 1:
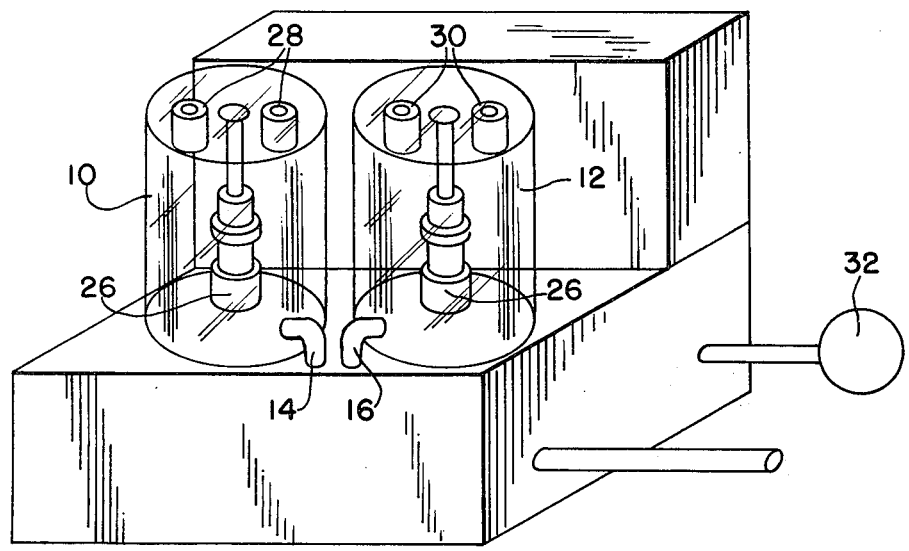
FIG. 1 is a view illustrating an arrangement of the apparatus for the multi-patient system.
Figure 2:
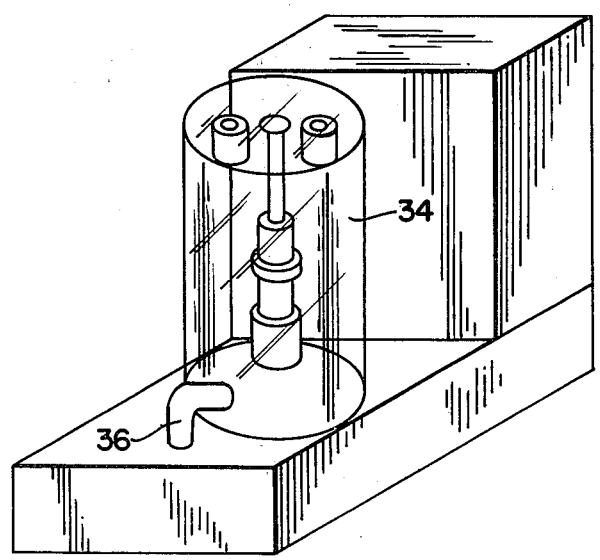
FIG. 2 is a similar view illustrating the single patient system.
Figure 3:
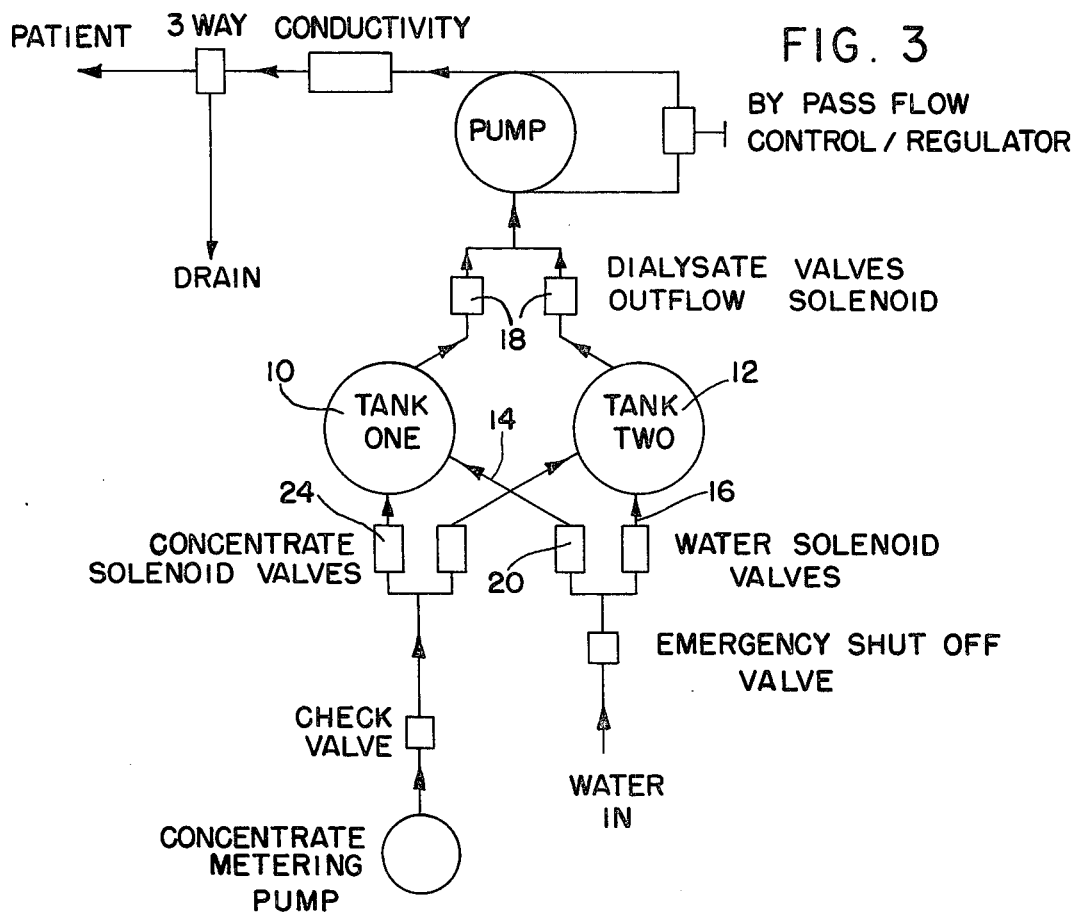
FIGS. 3 and 4 are diagrams or flow sheets of FIGS. 1 and 2 respectively.
Figure 4:
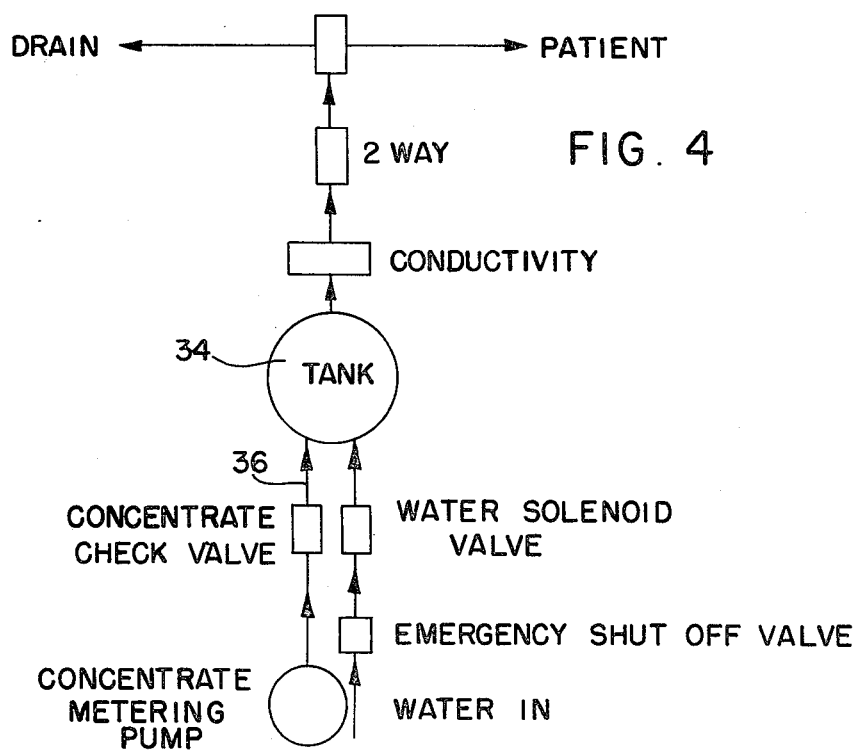

Referring to FIG. 1, there is shown therein a plurality of dialysate tanks, in this case two, these being indicated at 10 and 12. These tanks are connected at 14 and 16 to a water supply e.g. a tap, and to a concentrate supply which is in form of any kind of container preferably as received from the manufacturer. These tanks are interconnected by means of directional valves 18. The tanks are duplicates and operate in the same way but in general one tank is operating to supply the patient while the other one is being filled.

These tanks are preferably of clear plastic material. A solenoid valve 20 controls the flow of water into tank e.g. 10. Also connected to this tank is a solenoid valve 24 which controls the concentrate flow into the same tank.

Inside each tank there is a float 26 to operate a pair of float switches 28–30, each of which has a high and low limit operating means. When the low limit switch is activated by the float, it in turn activates the concentrate solenoid valve 24 and the water valve 20 and flow into the tank commences.

One example of the relationship of water to concentrate flow is 34 to 1 but the mix cycle is not predicated on the time factor but on the volume factor. Thus when the solenoid for water and concentrate open to start flow, the water will flow in at a rate to produce approximately a liter e.g. in tank 10 and simultaneously the concentrate valve 24 opens and admits concentrate at about 30 cc or 1/24 part of a liter. The concentrate pump 32 is cycled to terminate its action well before the water stops flowing, to get the best mix possible. When the float 26 reaches its upper level, the tap water is turned off and the directional valve 18 is opened to a circulating pump to the patient.

The other pump etc., operates in the same way but alternately. In other words when the low limit valve in tank 10 is actuated to stop the flow to the patient, the water and concentrate inlet valves having been closed all this time during operation of flow of dialysate to the patient, then the other tank which has been filling and proportionally mixing is then automatically put into operation to the patient, and this action continues as long as may be required so that there is no interruption to the hemodialysis treatment. At the same time, ten separate patients may all be simultaneously treated by the single apparatus so far described.

By using the relatively small tanks, e.g. the single liter tanks 10 and 12, and small high capacity pumps, a minature portable system is enabled to supply a single patient or any number to ten or more. At the one patient demand level, a one liter tank would empty about every two minutes; at the ten patient demand level, each tank would empty about every 12 seconds. The speed of cycling is limited only by the circulating pump capacity to empty the tanks. The relay logic for the filling, switching, and emptying function and various fail-safe devices also is performed by latching type relays so that the system has a memory and will not malfunction if the supply power is interrupted or the voltage fluctuates severly. Conventional instrumentation to determine the conductivity of the output with bypass to drain, audio and visible alarms, etc., are incorporated as part of the relay control assembly.

THE SINGLE PATIENT SYSTEM

In this case a single tank 34 is utilized and this tank proportionately mixes the dialysate and dilutes one part hemodialysis liquid concentrate with 34 parts of tap water in the tank 34. The metered concentrate enters the mixing tank as at 36 only after the tap water has started to flow, thus insuring thorough mixing. The normal fill time for the one liter batch is 10 to 20 seconds at a tap water pressure of 10 to 60 psi and since these batches are mixed at atmospheric pressure they are deaerated simply and effectively.

The proportionate operation is fully automatic and fail-safe. The conductivity monitor controls the flow of mixed proportionated dialysate to the coil canister in negative-pressure reservoir. Emptying of the tanks would take about two to three minutes as accomplished through solenoid valve float switches as above-described as to the multiple system with the difference that when the float reaches the bottom switch and shuts off the flow to the patient at the same time turning on the water supply and concentrate supply, a stop period of two seconds is all that is necessary to refill the tank and once more put the device into operation insofar as the patient is concerned. This short interruption of the supply to the patient has no effect or any danger at all to the patient, and therefore it will be seen that the operation is substantially continuous with a few seconds hiatus during which the tank is refilled and the concentrate is reproportioned in the tap water preparatory to the next round of operation of two or three minutes. In addition of course appropriate drainage is provided.

I claim:

1. In a hemodialysis proportioning system, a dialysate tank, a source of dialysate concentrate, a source of water, a water supply valve opening and closing said water source to said tank, a dialysate concentrate supply valve opening and closing said dialysate concentrate source to said tank, a metering pump means connected in series with said dialysate source and said dialysate supply valve for feeding a measured amount of dialysate concentrate to said tank, a high level sensing means for sensing a predetermined high liquid level within said tank and a low level sensing means for sensing a predetermined low liquid level within said tank, a dialysate outlet valve opening and closing the dialysate from said tank to the patient, separate means responsive to said low level sensing means when the predetermined low liquid level is sensed for opening said water supply valve and said dialysate concentrate supply valve, for closing said dialysate outlet valve and for cycling said dialysate metering pump to meter a predetermined volume of dialysate concentrate to said tank, said separate means being responsive to said high level sensing means when said high liquid level is reached to open said dialysate outlet valve and to close said water and dialysate concentrate supply valves.

2. The apparatus according to claim 1 wherein said high level sensing means and said low level sensing means comprise high and low limit switches respectively and a float for actuating said switches when predetermined high and low liquid levels are reached.

3. In a hemodialysis proportioning system comprising a plurality of tanks, an outlet from said tanks to direct dialysate to a patient or to a plurality of patients, directional dialysate outflow valves for each tank supplying dialysate selectively alternatively with respect to said dialysate outlet, a float in each tank, upper and lower limit switches in each tank, said floats actuating the switches, a dialysate concentrate supply, a water supply, a metering pump means for pumping a metered amount of the dialysate concentrate from said concentrate supply alternately to said tanks, a first concentrate supply valve connected between one of said tanks and said pump means and a second concentrate supply valve connected between the other of said tanks and said pump means, a first water supply valve connected between said water supply and one of said tanks, a second water supply valve connected between said water supply and the other of said tanks, said first concentrate supply valve and said first water supply valve being actuated in response to the actuation of said upper limit switch in said one tank to shut off said concentrate and said water supply to said one tank, and being responsive to the actuation of said lower limit switch of said one tank to open said concentrate supply and water supply to said one tank, said second concentrate supply valve and said second water supply valve being actuated in response to the actuation of said upper limit switch in said other tank to shut off said concentrate supply and water to said second tank, and being responsive to the actuation of said lower limit switch in said other tank to open the concentrate supply and water supply to said second tank, said directional outflow valve for one tank being responsive to the actuation of the lower limit switch in said one tank to close off the outflow of dialysate from said one tank to said patient, while said directional outflow valve from said other tank is simultaneously responsive to the actuation of the lower limit switch in said one tank to open the outflow of said other tank to the patient, and alternately said directional outflow valve for the other tank being responsive to the actuation of the lower limit switch of the other tank to close off the outflow of dialysate from said other tank to said patient while said directional outflow valve from said one tank is simultaneously responsive to the actuation of the lower limit switch in said other tank to open the outflow of said one tank to the patient, said metering pump means being cycled after the opening of one of said first and second water supply valves to pump a metered amount of dialysate concentrate.

4. In a hemodialysis proportioning system comprising a plurality of tanks, an outlet from said tanks to direct dialysate to a patient or to a plurality of patients, directional dialysate outflow valves for each tank supplying dialysate selectively alternatively with respect to said dialysate outlet, an upper level sensing means and a lower level sensing means in each tank for sensing predetermined upper and lower liquid levels respectively within each tank, a dialysate concentrate supply, a water supply, a metering pump means for pumping a metered amount of the dialysate concentrate from said concentrate supply alternately to said tanks, a first concentrate supply valve connected between one of said tanks and said pump means and a second concentrate supply valve connected between the other of said tanks and said pump means, a first water supply valve connected between said water supply and one of said tanks, a second water supply valve connected between said water supply and the other of said tanks, said first concentrate supply valve and said first water supply valve being actuated in response to the actuation of said upper level sensing means in said one tank to shut off said concentrate and said water supply to said one tank, and being responsive to the actuation of said lower level sensing means of said one tank to open said concentrate supply and water supply to said one tank, said second concentrate supply valve and said second water supply valve being actuated in response to the actuation of said upper level sensing means in said other tank to shut off said concentrate supply and water to said second tank, and being responsive to the actuation of said lower level sensing means in said other tank to open the concentrate supply and water supply to said second tank, said directional outflow valve for one tank being responsive to the actuation of the lower level sensing means in said one tank to close off the outflow of dialysate from said one tank to said patient, while said directional outflow from said other tank is simultaneously responsive to the actuation of the lower level sensing means in said one tank to open the outflow of said other tank to the patient, and alternatively said directional outflow valve for the other tank being responsive to the actuation of the lower level sensing means of the other tank to close off the outflow of dialysate from said other tank to said patient while said directional outflow valve from said one tank is simultaneously responsive to the actuation of the lower level sensing means in said other tank to open the outflow of said one tank to the patient, said metering pump means being cycled to pump a metered amount of dialysate concentrate to the tank with open dialysate supply valve while water is being supplied to said tank to insure mixing of dialysate concentrate and water in the tank being filled.

* * * * *